United States Patent [19]

Karasz et al.

[11] Patent Number: 5,192,479
[45] Date of Patent: Mar. 9, 1993

[54] METHOD FOR DISPERSING MISCIBLE POLYMERIC COMPONENTS

[75] Inventors: Frank E. Karasz, Amherst, Mass.; Wansoo Huh, Dayton, Ohio

[73] Assignee: The B.F. Goodrich Company, Akron, Ohio

[21] Appl. No.: 832,100

[22] Filed: Feb. 6, 1992

Related U.S. Application Data

[62] Division of Ser. No. 443,294, Nov. 29, 1989, Pat. No. 5,106,918.

[51] Int. Cl.$^5$ .................. B29C 47/88; B29C 71/00; B32B 31/20; C08J 5/00
[52] U.S. Cl. ..................... 264/171; 264/211.12; 264/331.13; 264/348
[58] Field of Search .............. 264/171, 211.12, 331.13, 264/348

[56] References Cited

U.S. PATENT DOCUMENTS

| | | | |
|---|---|---|---|
| 4,444,817 | 4/1984 | Subramanian | 264/171 |
| 4,722,595 | 2/1988 | Siol | 350/353 |
| 4,731,417 | 3/1988 | Miyata | 525/200 |
| 4,772,506 | 9/1988 | Siol et al. | 428/212 |
| 4,777,492 | 10/1988 | Ohnishi et al. | 346/1.1 |
| 5,108,844 | 4/1992 | Blemberg et al. | 264/171 |

*Primary Examiner*—Jacob Ziegler
*Attorney, Agent, or Firm*—Thoburn T. Dunlap

[57] ABSTRACT

A method for dispersing a second polymer within a first polymer is disclosed, the polymers being mutually miscible and when blended exhibit lower critical solution temperature (LCST) type behavior. The first and second polymers are blended together at a temperature for easy processing and then phase separated at a temperature above the LCST of the blended polymer pair. The phase separated polymers are then cooled to a temperature wherein the polymer pair become fixed in the phase separated state.

7 Claims, 4 Drawing Sheets

ISOTHERMAL COMPOSITION–COMPOSITION PHASE DIAGRAM OF CPVC/AN-BD AT 150°C & 170°C

- ● TWO PHASE AT 150°C & 170°C
- ⊕ SINGLE PHASE AT 150°C & 170°C
- ◐ TWO PHASES AT 150°C & SINGLE PHASE AT 170°C
- ◑ SINGLE PHASE AT 150°C & TWO PHASES AT 170°C
- ◀ TWO PHASE AT 150°C
- ◁ SINGLE PHASE AT 150°C
- ▶ TWO PHASES AT 170°C
- ▷ SINGLE PHASES AT 170°C

METHOD FOR DISPERSING MISCIBLE POLYMERIC COMPONENTS

This is a division of parent application Ser. No. 07,443,299 filed on Nov. 29, 1989, now U.S. Pat. No. 5,186,918.

BACKGROUND OF THE INVENTION

1. Field of the Invention

This invention relates to miscible blends of polymeric compositions. Particularly, this invention relates to miscible blends of thermoplastic and elastomeric compositions having lower critical solution temperature (LCST) behavior and to methods of utilizing this phenomenon to enhance the properties of such compositions. More particularly, the present invention relates to miscible blends of chlorinated polyvinyl chloride and copolymers of acrylonitrile-butadiene such that blends of the two manifest LCST behavior in a practically achievable temperature range.

2. Background of the Art

Chlorinated polyvinyl chloride (CPVC) has become an important specialty polymer due to its high glass transition temperature, high heat distortion temperature, chemical inertness and outstanding flame resistance. Typically, commercial CPVC has in excess of about 57 percent (by weight) chlorine and can be prepared by well-known techniques, such as by the suspension chlorination of polyvinyl chloride, for example. The CPVC resins so-made can be processed and formed by conventional methods such as by milling, calendering, extruding, laminating, molding and the like. However, a well-known undesirable characteristic of CPVC is that as the chlorine content of the polymer is increased, the resin becomes more difficult to process. The increased chlorine content results in a hardening or stiffening of the polymer so that its melt flow is greatly reduced at a given temperature. Consequently, the polymer is difficult to process, mold and shape without the addition of modifying additives. Moreover, another well-known undesirable property of CPVC is that it has inherently low impact properties.

To overcome these problems it has been proposed to add to the CPVC modifying additives such as processing aids and impact modifiers. A processing aid is used in melt blending CPVC resin to hasten fusion, to smooth out the otherwise rough texture of the resin, and to soften the resin so that it is uniformly melt blended within an acceptably short period of time. Also, since the end use product must have desirable impact strength, impact modifiers are also essential to a CPVC composition. These efforts, however, have ordinarily proven unsatisfactory because any improvement achieved in one property has frequently been accomplished through the undue sacrifice of other desirable properties.

For example, impact modifiers are incompatible or semi-compatible discontinuous domains of rubbery-type elastomers that are homogeneously dispersed throughout a continuous thermoplastic phase. For optimum performance, the impact modifier must resist the formation of a single phase system within the thermoplastic which it is dispersed. The utilization of the elastomeric impact modifiers contribute little, if any, improvement in processability, and sometimes even increase the melt elasticity of the CPVC composition. Generally, most impact modifiers and processing aids, when conventionally utilized in conjunction with one another do not provide either sufficiently high impact strength or desirable processability, or both, without undue sacrifice of other desirable physical properties. Thus, matching of impact modifiers and processing aids for compatibility and optimum performance is a trial and error task that is usually difficult and time consuming.

For the purpose of developing new materials with desirable properties, miscibility in polymer blends has been laboriously studied. In one approach, it has been proposed to prepare blends of CPVC with other polymers to maximize CPVC's processing characteristics and/or physical properties. While miscible blends have been reported in the literature from time to time, it is well-known that non-miscibility is the rule and miscibility and even partial miscibility is the exception. The prediction of miscibility between polymer pairs is still an art in infancy. Miscibility is believed to be dependent upon a number of factors that include interactions between functional moieties in or pendant from one or more of the polymers, hydrogen bonding, and the like. Various suggestions have appeared for assisting in the selection of miscible polymer pairs including an application of Flory's equation of state as set forth by L. P. McMaster, *Macromolecules*, 6, P. 760, (1973).

Other suggestions for useful tools in assessing miscible polymer pairs have included normal or three-dimensional solubility parameters, inverse gas chromatography, crystalization characteristics of polymer blends, or evaluation of glass transition temperature shifts, as suggested by L. M. Robeson, *Polymer Engineering and Science*, 24, p. 589 (June 1984). The statement that the prediction of miscible polymer pairs is an art rather than a science, is demonstrated by, for example, the fact that chlorinated polyethylene having 42 weight percent chlorine is miscible in polyvinyl chloride, while chlorinated polyethylene having a chlorine content less than 42 percent is immiscible in polyvinyl chloride as shown by Robeson, supra at p. 588.

The occurrence of lower critical solution temperature (LCST) behavioral phenomena is commonly associated with the miscibility of polymers. Polymer blends that exhibit LCST-type behavior exist as a miscible blend P (i.e., single phase) below its LCST, and separates into polymer constituents $P_1$ and $P_2$ (i.e., two phases) above its LCST.

Miscible blends of polymers have found utility in providing enhanced properties such as plasticization, tensile strength, melt processibility, and enhanced resistance to heat distortion. However, while miscible blends may be utilized to enhance one or perhaps two of the foregoing properties, those skilled in the art have long sought for a dual function modifier having sufficient miscibility to function as a processing aid during processing and at the same time possessing sufficient properties to function as an impact modifier in the finished end product. A desirable dual modifier should impart miscibility for good processability and have the capability to induce incompatibility for good impact properties in the final product. However, at first glance, it would seem that these properties are mutually exclusive of one another. Accordingly, there is a need for a composition and method therefor to solve these problems.

SUMMARY OF THE INVENTION

It is therefore an aspect of the present invention to provide a rigid CPVC plastic formulation of exceptional impact resistance, which formulation is easily processable.

It is another aspect of the present invention to provide a miscible blend of CPVC and a flow enhancing polymer.

It is still another aspect of the present invention to provide a method for dispersing one polymer throughout another polymer.

It is a further aspect of the present invention to provide a composition comprising an elastomer dispersed throughout a thermoplastic.

It is a still further aspect of the present invention to provide a composition comprising a thermoplastic dispersed throughout an elastomer.

According to the invention, these and other aspects can be achieved by a process comprising: selecting a first and second polymer which are mutually miscible and which exhibit LCST-type behavior; mixing said first and second polymers at a temperature below the phase boundary containing an LCST (LCST phase boundary) of the polymer blend and above the glass transition temperature-blend composition curve (Tg composition line) of the polymer components or above the Tg of the higher Tg polymer component, to achieve a homogeneous blend; heating the homogeneous blend at a temperature above its LCST phase boundary to effect a phase separation wherein said first and said second polymers demix and form a dispersion comprising a dispersed second polymer phase within a continuous first polymer phase; and cooling said dispersion below its Tg composition line or below the Tg of the lower Tg polymer component wherein said dispersed and said continuous polymer phases become irreversibly fixed.

DETAILED DESCRIPTION OF THE INVENTION

The present invention is particularly focused on polymer blends exhibiting LCST-type behavior. By LCST-Type behavior we mean that a polymer blend P exhibits a phase boundary with a temperature minimum called the LCST in which the region above the boundary exists as two phases and the region below the boundary therefore exists as a single phase. Such a polymer blend maintains miscibility at processing temperatures below its LCST phase boundary and, accordingly, is easily processable. However, at temperatures above its LCST phase boundary, miscible blend P undergoes phase separation into two phases which will predominately contain its component polymers, $P_1$ and $P_2$. For any given composition, the phase separation temperature must be above the glass transition temperature-blend composition curve (Tg composition line) of the blend (see FIG. 1).

Figure 1:
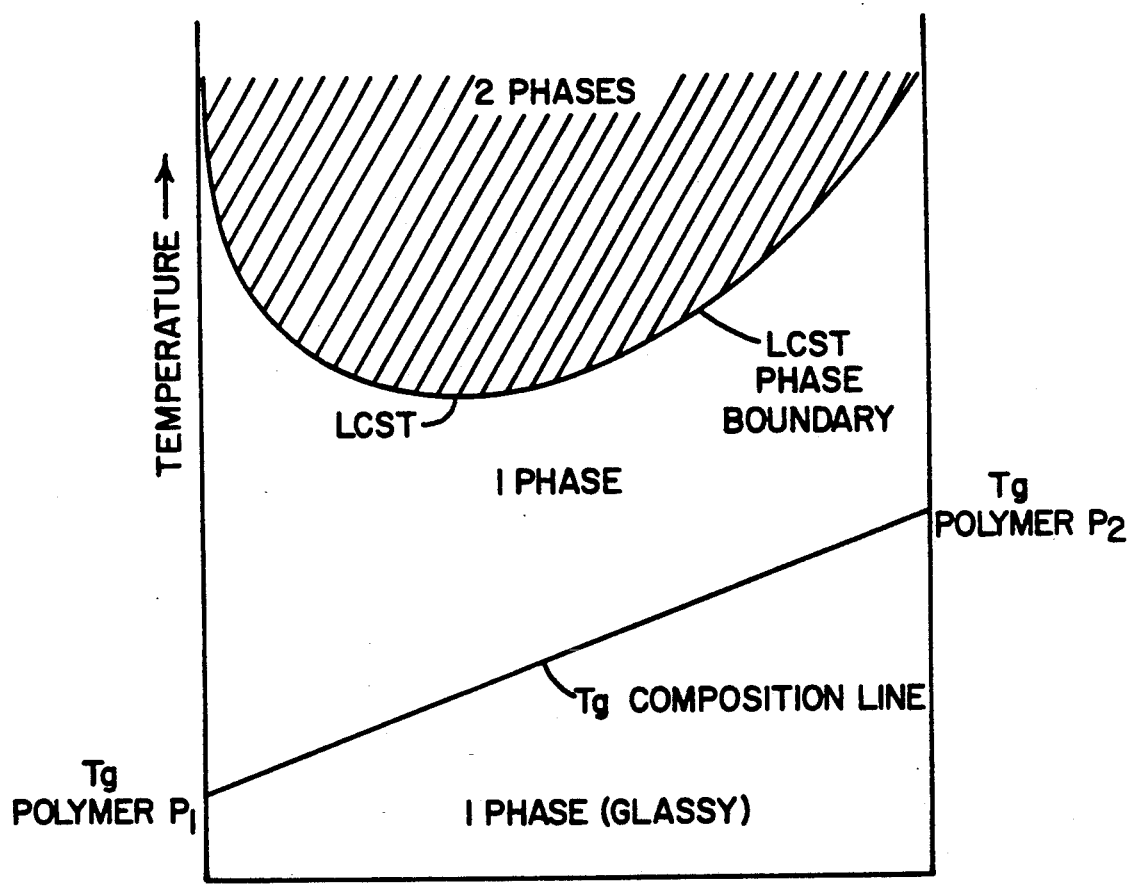
FIG. 1 shows a generalized phase diagram for a polymer blend exhibiting a phase boundary with a lower critical solution temperature (LCST) and a glass transition temperature-blend composition curve characteristic of the blends of the present invention.

In many systems, the separation of components becomes fixed upon cooling. This phenomenon can be utilized to synthesize polymers with improved physical properties. FIG. 1 illustrates a typical phase diagram of LCST-type behavior for a polymer blend P.

A resin composition according to the present invention is a miscible two component blend in which each component is a homopolymer or copolymer. As used herein, the term copolymer is also meant to include any polymer containing two or more different monomers such as, for example, terpolymers and the like. The components are selected so as to provide a thermoplastic-elastomeric, thermoplastic-thermoplastic, or elastomeric-elastomeric blend which displays LCST-type behavior. Preferably, the compositions are selected so that in the phase separated state one component exists as a continuous phase while the other component exists as a dispersed phase. Generally, this can be accomplished by utilizing the continuous phase component (majority phase) in excess over the dispersed phase (minority phase) component (i.e., the continuous phase component makes up at least about 50% by weight of the polymer blend). For impact modified thermoplastics, we refer to the thermoplastic component as the continuous phase and the elastomeric component as the dispersed phase. This invention also comprehends embodiments wherein the elastomeric phase is the continuous phase and the thermoplastic is the dispersed phase. Of course, it should be noted that thermoplastic-thermoplastic and elastomeric-elastomeric compositions are also contemplated within the scope of this invention.

In accordance with the present invention, one must start by selecting a polymer pair that exhibits an LCST phase diagram as exemplified in FIG. 1. Polymer blend(s) P that meets this selection criteria can be discovered systematically by keeping one polymer constituent the same while varying the nature, and in the case of a copolymer, the relative comonomer composition, and finally the overall blend composition. As used herein, the term polymer blend is meant to include copolymer blends and homopolymer/copolymer blends. Chances of finding blends that exhibit LCST-type behavior are increased by utilizing at least one copolymer constituent. Once miscibility is found, the system can be fine tuned with reference to its LCST by adjusting the comonomer composition of one or both of the polymer constituents in the blend. For example, if $P_1$ is a chlorinated thermoplastic homopolymer and $P_2$ is an elastomeric copolymer, constituent $P_1$ can be kept constant while the comonomer content and/or the amount of $P_2$ is varied until a miscible composition of LCST-type behavior is attained or not. Likewise, one can also vary the amount of the chlorine content of $P_1$ and/or the amount of $P_1$. Examples of polymer pairs that exhibit LCST-type behavior are disclosed in U.S. Pat. Nos. 4,722,595 and 4,731,417 which are hereby incorporated by reference.

Figure 2:
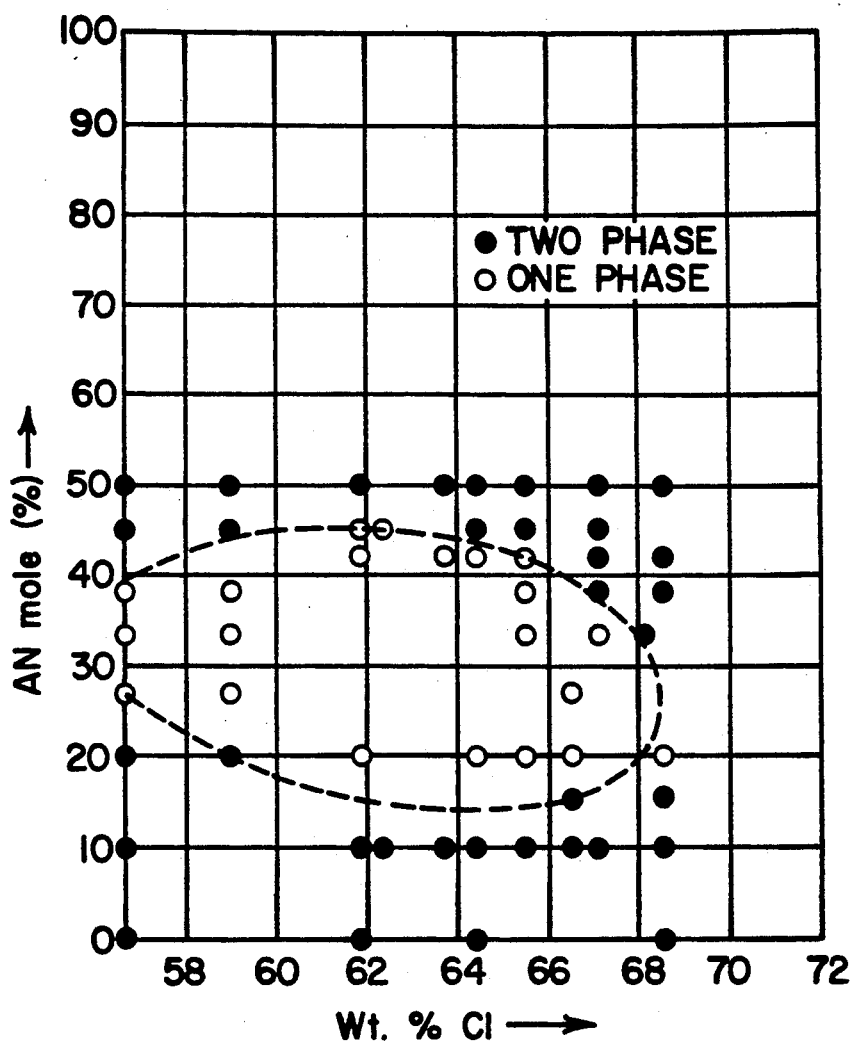
FIG. 2 shows the isothermal compositional phase diagram of chlorinated polyvinyl chloride/acrylonitrile-butadiene blends annealed at 150° C.

In the selection process for one embodiment of the invention, polymer constituents $P_1$ and $P_2$ are solubilized in a common solvent to achieve a homogeneous mixture of the two constituents. The homogeneous mixture of $P_1$ and $P_2$ is then precipitated by a second solvent in which the first solvent containing the dissolved polymers is soluble but in which the polymers P₁ and P₂ are not. The precipitant is then equilibrated at a temperature above the glass transition temperature(s) (Tg) of the individual constituents to facilitate homogeneous mixing. By the term glass transition temperature is meant the temperature at which an amorphous polymer or the amorphous regions of a partially crystalline polymer changes from a hard and relatively brittle condition to a more flexible or rubbery condition. During annealing it is generally necessary to work at temperatures under the LCST phase boundary (assuming one exists for the blend). At temperatures above the LCST phase boundary, the blend will exist in two phases giving false indications of immiscibility. Therefore, when confirming miscibility, it is important that the Tg's or the Tg composition line of the polymer components be below the LCST phase boundary of the blend. Measurement of the Tg's of polymer systems is described, for example, in *Thermal Characterization Techniques*, Slade et al, Marcel Decker Inc., New York (1970). After equilibration, the blend is cooled to room temperature. The miscibility of the blend can be confirmed by observing the glass transition(s). The appearance of a single Tg or a single Tg composition line is an indication that the blend is miscible. Immiscible blends, on the other hand, exhibit two Tg's characteristic of the Tg of each of the constituent polymers. Once miscibility is confirmed, a miscibility envelope for the constituent polymers can be established by varying the monomer content of the constituent polymers or copolymers and optimally annealing the blend above the Tg of the higher Tg component. FIG. 2 represents a miscibility envelope for a 50:50 mixture of CPVC and acrylonitrile-butadiene blends at 150° C. Blends that fall on or near the miscibility-immiscibility boundary (i.e., the broken line) can be evaluated for phase separation by systematically increasing the temperature and observing the blend with respect to its Tg behavior. The lowest temperature at which phase separation occurs is the LCST for that particular blend system. Once phase separation occurs, the polymer blend can be fixed in the phase separated state by rapid cooling from the heated phase to below the Tg composition line.

The location of the LCST phase separation temperature for polymer blend P, made up of polymer or copolymer constituents P₁ and P₂ can be influenced by a variation in one or more of the following parameters:

(a) By changing the proportions of the polymers P₁ and P₂ in the blend (b) By changing the molecular weight of constituent polymers P₁ and P₂; and (c) More generally, the phase separation temperature can also be changed in the case of one or both polymer constituents by changing the comonomer ratio in those constituents.

In some cases, the decomposition temperature of blend constituents will be below the LCST. In this regard, the thermal stability of the polymer constituents can be enhanced by the addition of well-known thermal stabilizers such as disclosed in the Encyclopedia of PVC. Vol. 2, pp. 45–141, published by Marcel Decker, Inc. (1985).

Particularly suitable in accordance with the present invention are polymer blends of CPVC and acrylonitrile-butadiene copolymers (AN-BD). Surprisingly, it has been discovered that certain blends of CPVC and AN-BD elastomers exhibit LCST-type behavior.

The CPVC polymers suitable for use in the miscible blends of this invention are readily available commercially or can be prepared by techniques disclosed in the literature such as described, for example, in U.S. Pat. Nos. 2,996,489; 3,100,762; 3,334,077; 3,334,078; 3,506,637; 3,534,013; 3,591,571; 4,049,517; 4,350,798; 4,377,459; 4,412,898; and 4,459,387. The chlorine content of the CPVC polymer typically can range from about 57 to 69 weight percent.

Similarly, the AN-BD elastomers suitable for use in the present invention are readily available commercially or can be prepared by well-known techniques. The typical AN-BD elastomer utilized herein contains from about 5 to about 50 weight percent acrylonitrile.

In accordance with the method of the present invention, polymeric articles can be produced by processing polymer blend P below its LCST phase boundary but above the Tg's for polymers P₁ and P₂. Such blends can be mixed on a two-roll mill, in an internal mixer such as a Brabender mixer or Banbury mixer, or in a twin-screw extruder. Blends may also be prepared by precipitation from a solvent and then melt-blending the precipitate using one of the above-disclosed techniques. In this way achievement of a homogeneous blend can be accomplished more easily. In a solution blending operation, the polymers to be blended are dissolved in a solvent in which the polymers are mutually soluble, generally at elevated temperature. The solution of polymers is then poured rapidly into a second solvent in which the first solvent containing the dissolved polymers is soluble but in which the polymers are not. A closely intermixed polymeric precipitate results which can be recovered using well-known techniques and conveyed to the melt-blending operation.

Subsequent to melt-blending, miscible blend P is then formed into the desired shaped article. The shaped article can be formed by known techniques such as, for example, injection molding, compression molding, pour molding, blow molding, and the like. Once the melt-blended miscible polymer blend is conveyed to the mold, the mold and its contents are then heated to above the LCST of the blend. Upon the occurrence of the desired amount of phase separation, the mold and its contents are cooled below the Tg of the lower Tg component to effect the locking in of the phase separated characteristics of the polymer system.

The composition of the present invention can contain various additives in addition to the miscible polymer components to enhance the properties of the miscible blend or the final shaped article products. For example, stabilizers, flame retardants, plasticizers and the like can be present so long as these additives do not adversely affect any desired property of the blend in the miscible or phase separated state.

The invention now being generally described will be better understood by reference to certain specific examples which are included herein for purposes of illustration only and are not intended to be limiting of the invention or any embodiment thereof.

EXAMPLE 1

Polymer blends meeting the conditions required by polymer blend P according to the present invention can be discovered deliberately and systematically.

To identify possible miscibility in and phase boundaries of CPVC/AN-BD blends, various 50:50 blends of CPVC and random copolymers of AN-BD were prepared by dissolving selected CPVC samples and selected AN-BD samples in the common solvent tetrahydrofuran (THF). The chlorine content of the CPVC (59.0 to 68.5 weight percent) and the acrylonitrile content of the AN-BD (10 to 51 mole percent) were varied systematically. Table 1 sets forth the compositions of the polymers used to prepare the blends. Each blend was stirred until completely dissolved and then precipitated in a ten-fold excess of methanol. The precipitated homogeneous blends were washed several times with fresh methanol to remove any residual THF and then dried at 65° C. for 72 hrs.

The miscibility behavior of each sample was studied by observing the glass transitions using a Perkin-Elmer DSC-4 Differential Scanning Calorimeter. The Tg's were determined from the locations of the maxima in plots of dCp/dT versus temperature (where Cp is heat capacity). In order to characterize the phase behavior, each blend was annealed at elevated temperature (150° C.) for 15 mins. in the DSC and then quenched down to a temperature below that of the lower component Tg in the blend. The DSC thermogram to determine the phase behavior of each blend was run at a heating rate of 20° C./min. The phase behavior of each sample was observed and plotted.

FIG. 2 represents the isothermal compositional phase diagram of the CPVC/AN-BD blends (50/50 weight percent) at 150° C. In this diagram, the X-axis represents the degree of chlorination of the CPVC copolymer expressed as weight percent chlorine and the Y-axis represents the mole fraction of acrylonitrile units in the AN-BD copolymer. The abscissa thus represents blends of PVC with AN-BD copolymer showing a miscibility window between 27 and 38 weight percent acrylonitrile, while the origin represents a PVC/polybutadiene blend. As the weight percent of chlorine increases (i.e., above the 57 weight percent chlorine content of PVC), the miscibility window for the CPVC/AN-BD blends enlarges (almost twice that of the PVC blend) until the chlorine content of the CPVC reaches 63 weight percent. At this composition, the maximum miscibility of the blend is found for the widest range of AN-BD with an acrylonitrile content between 20 and 44 mole percent. The broken line thus represents the boundary between the miscible and immiscible (e.g., single phase-two phase) regions of the diagram.

TABLE I

| Polymer Blend Components | | |
|---|---|---|
| | Wt. % Cl | |
| PVC | 56.7 | |
| CPVC- | | |
| 1 | 59.0 | |
| 2 | 61.9 | |
| 3 | 62.3 | |
| 4 | 63.7 | |
| 5 | 64.4 | |
| 6 | 65.5 | |
| 7 | 66.5 | |
| 8 | 67.1 | |
| 9 | 68.1 | |
| 10 | 68.5 | |
| | Wt. % AN | Mole % AN |
| AN-BD | | |
| 1 | 0 | 0 |
| 2 | 10 | 10 |
| 3 | 16 | 16 |
| 4 | 20 | 20 |
| 5 | 27 | 27 |
| 6 | 33 | 33 |
| 7 | 38 | 38 |
| 8 | 44 | 44 |
| 9 | 48 | 48 |
| 10 | 50 | 50 |

EXAMPLE 2

The quantitative phase behavior of miscible polymer blends is dependent upon temperature as well as the composition of the two blended polymers.

In this example, the temperature of the sample blends, generally of the same composition of Example 1, was increased to 170° C. for 5 mins. and then quenched to a temperature below the Tg of the two components. As in Example 1, the phase behavior of each sample was observed and plotted.

Figure 3:
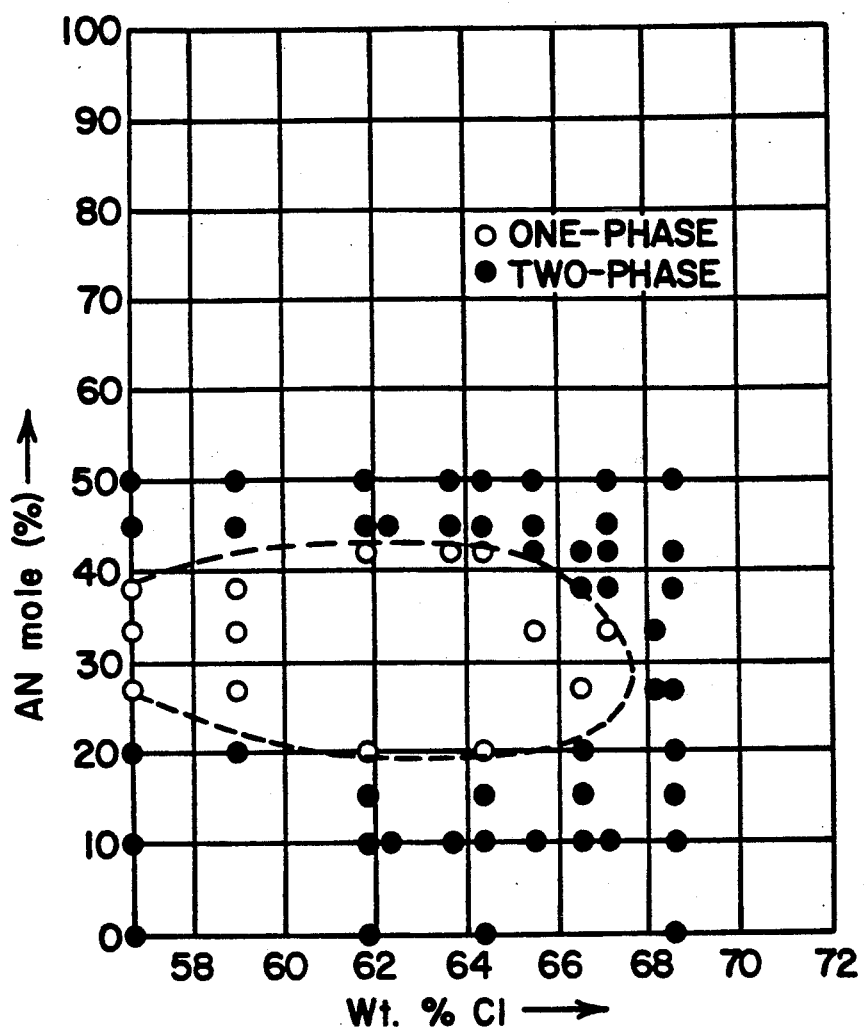
FIG. 3 shows the isothermal compositional phase diagram of chlorinated polyvinyl chloride/acrylonitrile-butadiene blends annealed at 170° C.

FIG. 3 represents the isothermal compositional phase diagram of the CPVC/AN-BD blends at 170° C. When the temperature is raised above 150°C., the region of miscibility decreases with increasing temperature.

Figure 4:
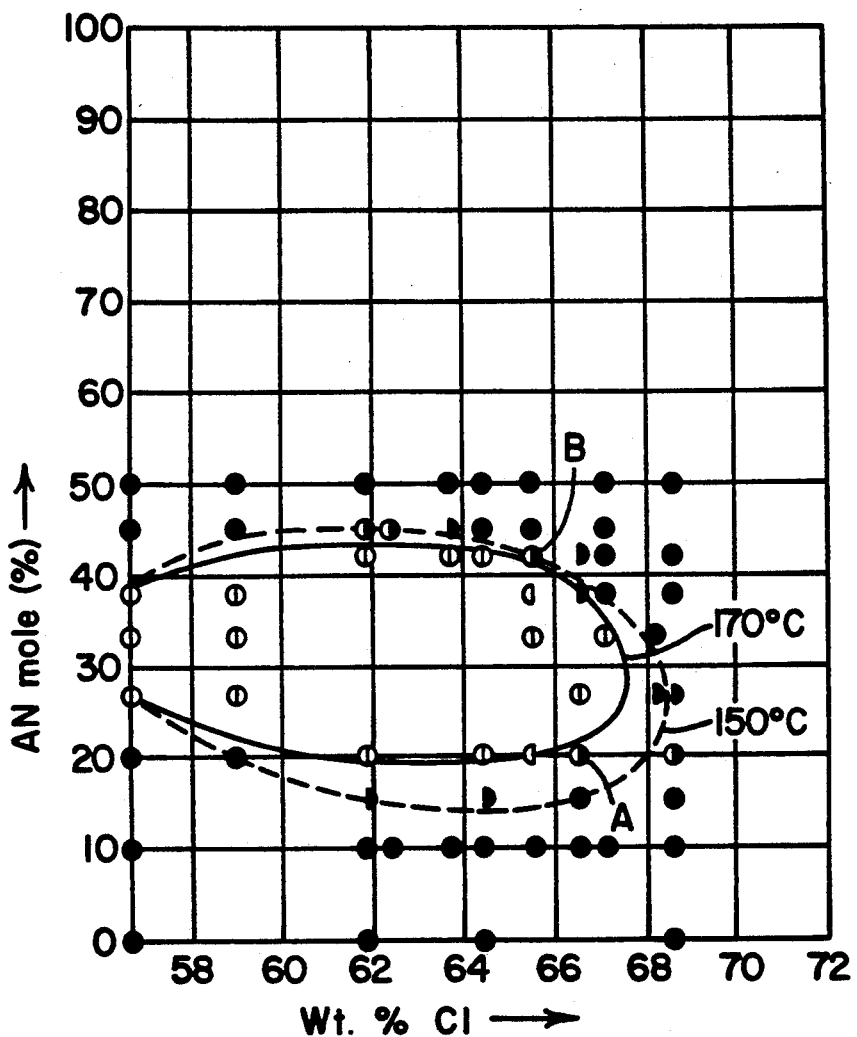
FIG. 4 shows the isothermal compositional phase diagram of chlorinated polyvinyl chloride/acrylonitrile-butadiene blends annealed at 150° C. with the isothermal compositional phase boundary for 170° C. superimposed thereon.

FIG. 4 compares the isothermal phase boundaries a 150° C. and 170° C. In order to illustrate the data points, the following legend has been employed. The left hand side and right hand side of each circle represent the phase behavior at 150° C. and 170° C., respectively. Filled sectors represent two phase behavior and unfilled sectors represent single phase behavior. Where data for a particular blend was available for only one temperature, the corresponding sector is shown. From these comparisons it can be readily seen that certain blends represented by points A and B, for example, that were miscible or at 150° C. (i.e., forming single phase systems) are immiscible at 170° C. (i.e., forming two phase systems). Accordingly, these compositions exhibit LCST behavior in this temperature interval.

FIG. 4 enables those skilled in the art to select further compositions which would display similar behavior. Furthermore, similar readily obtainable data for compositions other than the 50:50 blends exhibited here permit a still wider choice of blend and monomer compositions which would generally exhibit similar behavior.

EXAMPLE 3

A 50:50 mixture of the 20 weight percent AN, 67.1 weight percent CPVC/AN-BD copolymer of Examples 1 and 2 is annealed at about 150° until a homogeneous blend is achieved. The homogeneous blend is then injected into a bar shaped mold and heated to 170° C. for about 10 min. to effect phase separation. The mold and its contents are cooled to room temperature to yield a molded bar with a CPVC continuous phase having an elastomeric phase dispersed therein.

Although a 50:50 blend is utilized, the CPVC becomes the continuous phase because the AN-BD elastomer, being much more mobile (i.e., lower Tg) than CPVC, would coagulate and form droplets, i.e., becomes the dispersed phase in the less mobile CPVC continuous phase.

What is claimed is:

1. A method of shaping a plastic article comprising the steps of:
    Selecting a first and second polymer which are mutually soluble at a temperature above the Tg of the higher Tg polymer component and which blend exhibits a lower critical solution temperature (LCST) above the Tg of the higher Tg polymer component;

Blending said first and second polymer at a temperature above the Tg composition line of said polymer pair and below the LCST phase boundary of the resulting miscible polymer blend;

Shaping said miscible polymer blend into a desired article;

Heating the shaped article to a temperature above the LCST of its component blended polymers to effect a phase separation of said component blended polymers; and Cooling said shaped article to a temperature at least below the Tg composition line of the polymer pair wherein the polymers become irreversibly fixed in the phase separated state.

2. The method of claim 1, wherein said first polymer is a thermoplastic and said second polymer is an elastomer.

3. The method of claim 1, wherein said first polymer is an elastomer and said second polymer is a thermoplastic.

4. The method of claim 1, wherein said first polymer is a thermoplastic and said second polymer is a thermoplastic.

5. The method of claim 1, wherein said first polymer is an elastomer and said second polymer is an elastomer.

6. The method of claim 2, wherein said first polymer is chlorinated polyvinyl chloride.

7. The method of claim 2 wherein said second polymer is a random copolymer of acrylonitrile-butadiene.

* * * * *